United States Patent [19]
Haushalter et al.

[11] Patent Number: 5,705,695
[45] Date of Patent: Jan. 6, 1998

[54] QUATERNARY ZINTL COMPOSITION $(Et_4N)_4[Au(Ag_{1-x}Au_x)_2Sn_2Te_9]$

[75] Inventors: Robert C. Haushalter, Little York; Sandeep S. Dhingra, Robbinsville, both of N.J.

[73] Assignee: NEC Research Institute, Inc., Princeton, N.J.

[21] Appl. No.: 769,720

[22] Filed: Dec. 18, 1996

[51] Int. Cl.[6] ............ C07C 209/68; C07C 211/63
[52] U.S. Cl. ............ 564/281; 75/228; 75/230; 75/244; 106/1.26; 106/286.2; 106/286.4; 420/579; 420/589; 423/23; 423/24; 423/27; 423/32; 423/42; 423/364; 423/508; 556/28; 556/81; 556/87; 564/295; 564/296

[58] Field of Search ............ 420/579, 589; 106/1.26, 286.2, 286.4; 75/228, 230, 244; 423/23, 24, 27, 32, 42, 364, 508; 556/28, 81, 87; 564/295, 296, 281

[56] References Cited

U.S. PATENT DOCUMENTS 5,368,701  11/1994  Warren et al. ............ 204/59 OM

*Primary Examiner*—Peter O'Sullivan

[57] ABSTRACT

The quaternary Zintl material $(Et_4N)_4[Au(Ag_{1-x}Au_x)_2Sn_2Te_9]$ that contains 1-D semiconducting chains composed of four metallic elements is prepared by treating ethylenediamine extracts of a pentanary K—Au—Ag—Sn—Te alloy with $Et_4NI$.

6 Claims, 1 Drawing Sheet

QUATERNARY ZINTL COMPOSITION $(ET_4N)_4[AU(AG_{1-x}AU_x)_2SN_2TE_9]$

FIELD OF THE INVENTION

The present invention relates to a novel quaternary Zintl composition, $(Et_4N)_4[Au(Ag_{1-x}Au_x)_2Sn_2Te_9]$, where $Et_4N$ is tetraethylammonium and $x=0.32$, and to the method of its preparation.

BACKGROUND OF THE INVENTION

In the early 1930's, Zintl and coworkers showed that the electrolysis of certain main group, main group alloy, and intermatallic phases could produce metal polyanions in the catholyte. Through the potentiometric titrations of liquid ammonia solutions of these salt-like intermatallic compounds, and exhaustive extractions of alkali metal alloys of the heavier group 14 and 15 elements, they were able to deduce the existence of $Sn_9^{4-}$, $Pb_9^{4-}$, $Pb_7^{4-}$, $As_3^{3-}$, $As_7^{3-}$, $Sb_7^{3-}$, $Sb_3^{3-}$, $Bi_7^{3-}$, $Bi_5^{3-}$, and $Bi_3^{3-}$ but apparently did not isolate crystalline derivatives of these species to confirm their findings. These metal polyanions, which have come to be known as Zintl phases, are unique in that they have no exopoloyhedral ligands at the vertices and so can easily form metal—metal bonds, which make them ideal precursors for the preparation of conducting and semiconducting films and solids by topochemical or bulk oxidations. Such films might have a variety of uses, including use as coatings. The novel polyanion of the present invention should have the same uses.

The term Zintl phase has often been used to define an intermetallic compound comprising one element of the alkali and/or alkaline earth metals and one or more elements from the main group elements. It will be used herein to define a compound that comprises an organic cation and a polyanion involving a metal-to-metal bond of atoms of the same or different metals of the main group or transition group of metals. Moreover, as used herein, tin and tellurium are considered to be main group metals while silver and gold are considered to be transition metals. Such a polyanion will also be referred to as a Zintl anion.

Several chemical approaches have been developed over the last two decades to prepare one-dimensional (1-D) conducting materials such as platinum chain compounds, the salts of organic donor molecules, and transition metal chalcogenides. In particular, there was begun a study designed to determine the possibility, via suitable structural modifications or elemental substitutions, of introducing unpaired electrons into closed-shell, low-dimensional Zintl phase materials thereby increasing their electrical conductivity. In several cases, the structures were found to achieve a closed-shell electronic configuration by undergoing site-specific elemental substitutions (e.g., $K_9GeIn_9Sb_{22}$) or forming exceedingly complex structures (e.g., $K_8In_8Ge_5As_{17}$ or $K_5In_5Ge_5As_{14}$). Likewise, several binary and ternary one-dimensional (1-D) Zintl anions such as $InGeTe^{4-}$, $Hg_2Te_5^{2-}$, $Hg_3Te_7^{4-}$, $Hg_2Te_4^{2-}$, $As_2Te_5^{2-}$- and $InTe_2$- possess structures consistent with closed-shell electronic configurations.

One particularly desirable type of 1-D conducting solid, which would be directly analogous to a microscopic copper wire surrounded by an organic polymer insulator, would be composed of chains of covalently bonded metals surrounded by insulating organic regions which would hinder electronic coupling between the molecular wires. The present invention provides a method for the preparation of such a conductive 1-D metal chain whose composition consists of four different elements surrounded by insulating organic material.

SUMMARY OF THE INVENTION

The proposed invention in one aspect is a novel quaternary Zintl composition $(Et_4N)_4[Au(Ag_{1-x}Au_x)_2Sn_2Te_9]$, where $Et_4N$ is tetraethylammonium and $x=0.32$, that contains one dimensional (1-D) semiconducting chains which include the four elements, gold, silver, tin and tellunium.

From another aspect the present invention is a process for preparing the novel quaternary Zintl composition by treating ethylenediamine extracts of a pentanary K—Au—Ag—Sn—Te alloy with tetraethylammonium iodide, $Et_4NI$.

The novel quaternary Zintl composition consists of 1-D chains of $Au(Ag_{1-x}Au_x)_2Sn_2Te_9^{4-}$ each of which contains a $(Au—Te—Te—Te)_\infty$, strand with approximately linear $Te_3^{3-}$ groups.

The magnetic susceptibility of the novel composition shows it to be weakly paramagnetic and nearly temperature independent down to 4 Kelvin.

DETAILED DESCRIPTION

Figure 1:
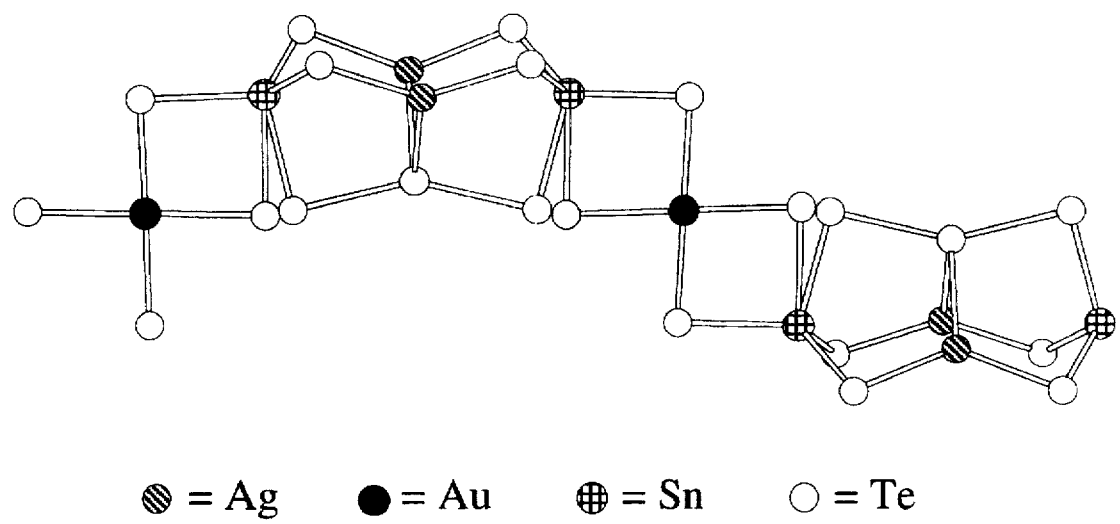
FIG. 1 shows the structure of the 1-D $Au(Ag_{1-x}Au_x)_2Sn_2Te_9^{4-}$ chain characteristic of the novel Zintl composition.

The novel Zintl composition, $(Et_4N)_4[Au(Ag_{1-x}Au_x)_2Sn_2Te_9]$, is advantageously prepared from the ethylenediamine extraction of a pentanary alloy of nominal composition $K_6AuAg_2Sn_2Te_9$. All manipulations are performed under argon, and the ethylenediamine (en) is distilled from a red solution of $K_4Sn_9$. The alloy of nominal composition $K_6AuAg_2Sn_2Te_9$ is prepared by fusing (at ca. 800° C.) stoichiometric amounts of $K_2Te$ (2,000 g, 9.72 mmol), Au(0.638 g, 3.24 mmol), Ag(0.698 g, 6.48 mmol), Sn (0.770 g, 6.48 mmol) and Te(2.894 g, 22.7 mmol) in a quartz tube under 1 atm argon for 1 minute with swirling. This homogenous melt is crushed to a fine powder and extracted with en (1 g alloy per 10 mL en) for 12–24 hr and filtered to remove undissolved solid. The dark red-brown extract is then added to a vial containing tetraethylammonium iodide, $Et_4NI$ (0.600 g, 2.33 mmol) in 9–10 mL en. Not all of the $Et_4NI$ dissolves. The first crystals of $(Et_4N)_4[Au(Ag_{1-x}Au_x)_2Sn_2Te_9]$, which form as tiny clumps of black intergrown blades, appear after approximately 2–3 months and continue to form for several months thereafter. The crystal quality, and to a lesser extent the yield, vary somewhat from reaction to reaction, but no other products have been detected and all crystals examined contain the four elements Au, Ag, Sn and Te. Although other alloy compositions were tried, including the composition $K_4AuAg_2Sn_2Te_9$, they give either no products or much lower yields.

Crystals of $(Et_4N)_4[Au(Ag_{1-x}Au_x)_2Sn_2Te_9]$ contain unprecedented linear 1-D semiconducting chains of composition $[Au(Ag_{1-x}Au_x)_2Sn_2Te_9]^{4-}$ which are shown in FIG. 1. The $[Au(Ag_{1-x}Au_x)_2Sn_2Te_9]^{4-}$ 1-D chains are separated in the solid state by $Et_4N^+$ cations (not shown) that act as insulating organic material between the chains. This is demonstrated by the fact that the closest interchain Te ... Te contact in the solid state structure of $(Et_4N)_4[Au(Ag_{1-x}Au_x)_2Sn_2Te_9]$ is 6.99 Å.

Still referring to FIG. 1, the Au atom has distorted square planar coordination while the Sn and Ag atoms possess tetrahedral and trigonal planar coordinations, respectively. Mixing of Au on the Ag sites is observed in the structure refinement at 32% substitution, which accounts for the $[Au(Ag_{1-x}Au_x)_2]$ where $x=0.32$ formulation of the compound. In addition, a small stoichiometric range is apparent from refinements of other crystals. This substitution is possible since bond distances for Au—Te and Ag—Te in trigonal planar coordination are very similar.

The prominent structural feature of the $Au(Ag_{1-x}Au_x)_2Sn_2Te_9^{4-}$ polyanion is the $\{—Au—Te—Te—Te—\}_\infty$ strand composed of Au atoms and approximately linear polytelluride trimer units (<Te—Te—Te=154.7°). The two symmetry equivalent Te—Te distances are 3.187(6) Å, which are longer than a typical Te—Te single bond distance (2.75 Å) but much shorter than the van der Waal Te . . . % contact of 4.0 Å. This suggests a bonding interaction of the type observed in previously characterized tellurides like $Te_{12}^{2-}$, $HgTe_{2-}$, $Cu_4SbTe_{12}^{3-}$, and $Au_2Te_{12}^{4-}$, as well as some other solid state tellurides. The observed Au—Te distance of 2.970(6) Å in $(Et_4N)_4[Au(Ag_{1-x}Au_x)_2Sn_2Te_9]$ is abnormally long compared with the Au—Te contacts near 2.65 Å found for $Au_2Te_{12}^{4-}$, $KAu_9Te_7^{4-}$, $K_2Au_4Te_4^{2-}$, and $Au_2Te_4^{2-}$. However, it should be noted that the Te atoms associated with the Au atoms in this structure have very large anisotropic thermal ellipsoids along the chain running parallel to the [010] direction. This observation is important to understanding the electronic structure of $(Et_4N)_4[Au(Ag_{1-x}Au_x)_2Sn_2Te_9]$ as will be discussed below.

Given the oxidation states of +1 for Ag and Au, +4 for Sn, and −2 for each Te, the charge on $Au(Ag_{1-x}Au_x)_2Sn_2Te_9$ is calculated to be −5 (which is in disagreement with the charge of −4 inferred from the crystal structure and elemental analysis). In this simplistic analysis and the close Te—Te contacts (3.19 Å) within each linear $Te_3$ trimer were neglected. Since there is one $Te_3$ trimer per formula unit $Au(Ag_{1-x}Au_x)_2Sn_2Te_9$, the charge is balanced if each $Te_3$ trimer is considered to possess a charge of −3. In general, the formal charge of −2 is associated with an oligomeric chain $Te_n^{2-}$ with Te—Te—Te bond angles of about 90°. Since a linear $Te_3$ trimer has three sigma orbitals made up of the p-orbitals, i.e., bonding (s), nonbonding (n), and antibonding (s*) levels, and since both the bonding and nonbonding levels can be used to accommodate electrons, the maximum charge to be associated with a linear $Te_3$ trimer is −4. Accordingly, the $Te_3^{3-}$ units in the $Au(Ag_{1-x}Au_x)_2Sn_2Te_9^{4-}$ chain have half-filled nonbonding levels, and therefore the $Au(Ag_{1-x}Au_x)_2Sn_2Te_9^{4-}$ chain should possess a half-filled band largely composed of the nonbonding levels. This observation is confirmed by the electronic band structure of an isolated $Au(Ag_{1-x}Au_x)_2Sn_2Te_9^{4-}$ chain calculated using the tight-binding extended Hückel method. The repeat unit cell of the $Au(Ag_{1-x}Au_x)_2Sn_2Te_9^{4-}$ chain has two formula units (hence two $Te_3^{3-}$ units), so the half-filled band is folded and the Fermi level occurs at the zone edge. This band is largely composed of the sigma nonbonding orbitals of the linear $Te_3$ trimers and the $x^2-y^2$ orbitals of the Au atoms. Since the $Au(Ag_{1-x}Au_x)_2Sn_2Te_9^{4-}$ chain has a partially filled band, one might expect $(Et_4N)_4[Au(Ag_{1-x}Au_x)_2Sn_2Te_9]$ to be metallic. However, since this band is a 1-D band, $(Et_4N)_4[Au(Ag_{1-x}Au_x)_2Sn_2Te_9]$ should be susceptible to a Peierls distortion which would open a band gap at the Fermi level.

Measurements indicate that the magnetic susceptibility of $(Et_4N)_4[Au(Ag_{1-x}Au_x)_2Sn_2Te_9]$ is essentially diamagnetic and this diamagnetism is nearly temperature independent down to 4K. The gram-susceptibility of $(Et_4N)_4[Au(Ag_{1-x}Au_x)_2Sn_2Te_9]$ is approximately $-2\times10^{-7}$ emu/g, which is similar to other chalcogenide semiconductors.

Since single crystals of $(Et_4N)_4[Au(Ag_{1-x}Au_x)_2Sn_2Te_9]$ typically grow to a maximum size of ca. 30×30×80 µg m³ and form mostly as clusters of crystals, conventional four probe electrical resistivity measurements were not possible. Resistivity data was therefore obtained by a microwave absorption technique (though confined to a small range of temperatures due to sample decomposition above about 80° C.) and showed that $(Et_4N)_4[Au(Ag_{1-x}Au_x)_2Sn_2Te_9]$ is a semiconductor with a band gap of 0.45(5)eV (extrapolated to 0K and assuming that the activated conductivity is purely intrinsic). Optical diffuse reflectance measurements, however, showed that $(Et_4N)_4[Au(Ag_{1-x}Au_x)_2Sn_2Te_9]$ has a band gap of 0.95(5)eV. It should be noted, however, that microwave absorption measures the total conductivity including extrinsic conductivity from defect-generated charge carriers, whereas optical diffuse reflectance measurements do not. Therefore, in order to explain the seemingly contradictive band gap values, one must conclude that the $Au(Ag_{1-x}Au_x)_2Sn_2Te_9^{4-}$ chains of $(Et_4N)_4[Au(Ag_{1-x}Au_x)_2Sn_2Te_9]$ have undergone a Peierls distortion above room temperature.

In summary, the extraction of a non-stoichiometric intermetallic mixture of alkali, late transition, and main group elements leads to a surprisingly complex 1-D chain material, $(Et_4N)_4[Au(Ag_{1-x}Au_x)_2Sn_2Te_9]$, with four different elements comprising the chain. There was for the first time prepared a 1-D Zintl anion with delocalized states which derived from the unique 1-D structure of the chains that contain unprecedented $Te_3^{3-}$ structural units. This 1-D Zintl anion exhibits a Peierls distortion which results in a semiconductor that is nearly diamagnetic. Based on the very large structural diversity of Zintl anions, it seems possible that other 1-D metal chain compounds could be prepared by this method. Accordingly, it should be understood that any and all such variations or modifications utilizing functionally equivalent elements to those described herein are intended to be included with the scope and spirit of the invention as defined by the appended claims.

What is claimed is:

1. The composition $(Et_4N)_4[Au(Ag_{1-x}Au_x)_2Sn_2Te_9]$ where $Et_4N$ is tetraethylammonium and x=0.32.

2. The composition of claim 1 further characterized by one-dimensional chains of $[Au(Ag_{1-x}Au_x)_2Sn_2Te_9]^{4-}$.

3. The composition of claim 3 further characterized in that each chain contains a $[Au—Te—Te—Te]_\infty$ strand.

4. The composition of claim 1 further characterized in that it is essentially diamagnetic and nearly temperature independent down to 4 Kelvin.

5. A process for preparing the composition of claim 1 that comprises the steps of:

fusing stoichiometric amounts of $K_2Te$, Au, Ag, Sn and Te to produce a pentanary alloy of nominal composition $K_6AuAg_2Sn_2Te_9$;

crushing said alloy into a fine powder;

extracting said powder with ethylenediamine;

filtering said extract; and adding said filtered extract to an ethylenediamine solution of $Et_4NI$.

6. The process according to claim 5 wherein said step of adding said filtered extract to said solution of $E_4NI$ results in the formation of crystals of $(E_4N)_4[Au(Ag_{1-x}Au_x)_2Sn_2Te_9]$.

* * * * *